United States Patent [19]

Ozaki et al.

[11] Patent Number: 5,073,911
[45] Date of Patent: Dec. 17, 1991

[54] COMPUTERIZED TOMOGRAPHIC APPARATUS

[75] Inventors: Masahiro Ozaki, Ootawara; Toshihiro Rifu, Nishinasunomachi, both of Japan

[73] Assignee: Kabushiki Kaisha Toshiba, Kawasaki, Japan

[21] Appl. No.: 707,276

[22] Filed: May 28, 1991

Related U.S. Application Data

[63] Continuation of Ser. No. 478,316, Feb. 12, 1990, abandoned.

[30] Foreign Application Priority Data

Feb. 13, 1989 [JP] Japan ................................. 1-31016

[51] Int. Cl.$^5$ .............................................. A61B 6/03
[52] U.S. Cl. ........................................ 378/17; 378/20; 364/413.15; 364/413.21
[58] Field of Search ................... 378/17, 15, 11, 14, 378/20, 901; 364/413.15, 413.16, 413.18, 413.21

[56] References Cited

U.S. PATENT DOCUMENTS

4,630,202 12/1986 Mori .
4,789,929 12/1988 Nishimura et al. ................ 378/20

*Primary Examiner*—Janice A. Howell
*Assistant Examiner*—David P. Porta
*Attorney, Agent, or Firm*—Finnegan, Henderson, Farabow, Garrett, and Dunner

[57] ABSTRACT

A patient platform of a gantry assembly is inserted into a scanning space of a housing dome. Within the dome around the space is provided an array of X-ray detectors arranged circumferentially. An X-ray tube is rotatably disposed outside the array. When the subject on the patient platform is inserted into the space, the X-ray tube irradiates X-rays in a fan shape toward the object. The X-ray detector array performs a nutation movement during the rotation of the X-ray tube so that the X-ray detectors on the X-ray irradiation path which is closer to the X-ray tube is outside the X-ray irradiation path. In this way, the object is continuously scanned in a helical manner with X-rays. The output of the detector array is supplied to an interpolation circuit. The interpolation circuit performs pre-processing on the output of the X-ray detector array, thereby providing projection data. The interpolation circuit interpolates to calculate desired projection data for a predetermined slice having a given projection angle by processing projection data for two slices located on both sides of the predetermined slice having the given projection angle and by processing the distances between the two slices and the predetermined slice.

10 Claims, 5 Drawing Sheets

COMPUTERIZED TOMOGRAPHIC APPARATUS

This application is a continuation of application Ser. No. 07/478,316, filed Feb. 12, 1990 now abandoned.

BACKGROUND OF THE INVENTION

1. Field of the Invention

The present invention relates to a computerized tomographic (CT) apparatus utilizing radiation rays such as X-rays, and, more particularly, to a CT apparatus which performs a helical scan to acquire projection data.

2. Description of the Related Art

CT apparatuses of the above mentioned type recently became popular since they can scan a wide examining region of an object to be examined in a short period of time. One example of such a CT apparatus is the computerized tomographic apparatus utilizing a radiation source disclosed in U.S. Pat. No. 4,630,202. The helical scan system moves the object in a given direction by permitting the patient platform of a gantry assembly on which the object is placed to slide in the direction of the body axis of the object, and rotates an X-ray tube around the object to continuously scan it. If it is assumed that the object is fixed, the locus of the movement of the X-ray tube relative to the object forms a helix. The pitch of the helix corresponds to the velocity of the patient platform. In contrast ordinary dynamic scan and multi-scan systems fix the object and the X-ray tube is always rotated within the same slice.

In reconstructing an image from projection data acquired by the helical scan, system projection data for one helical turn may be processed as one set of projection data corresponding to one slice of the image. In this case, however, since the data for a projection angle of 0° differs from that for a projection angle of 360° by a distance corresponding to the pitch of the helix, some inconsistency will naturally occur in image reconstruction. This is likely to cause an artifact, such as a streak on a reconstructed slice image. This artifact becomes more prominent as the distance corresponding to the pitch of the helix is increased to speed up data acquisition.

To prevent such shortcomings, according to the aforementioned United States patent, data from 0° to $(360+\beta)°$ is acquired as one set of projection data, and data from 0° to $\alpha°$ is smoothed using data from 360° to $\alpha°$ in order to eliminate the above inconsistency. This method, however, simply causes the data for 0° and the data for 360° to appear within the same slice, and does not cause data for the entire 360° to come within the same slice (plane). Therefore, the artifact cannot be eliminated completely.

SUMMARY OF THE INVENTION

It is an object of the present invention to provide a computerized tomographic apparatus capable of attaining a slice image with less artifact in reconstructing an the image from data acquired through a helical scan.

A computerized tomographic apparatus according to the present invention comprises scanner means for moving an object in one direction and rotating radiation rays within a plane intersecting this direction to perform a helical scan on the object to provide projection data, and interpolation means for interpolating projection data of a predetermined slice and having a given projection angle in accordance with projection data of two slices located on both sides of the predetermined slice and having given projection angles and distances between the two slices and the predetermined slice.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Figure 1:
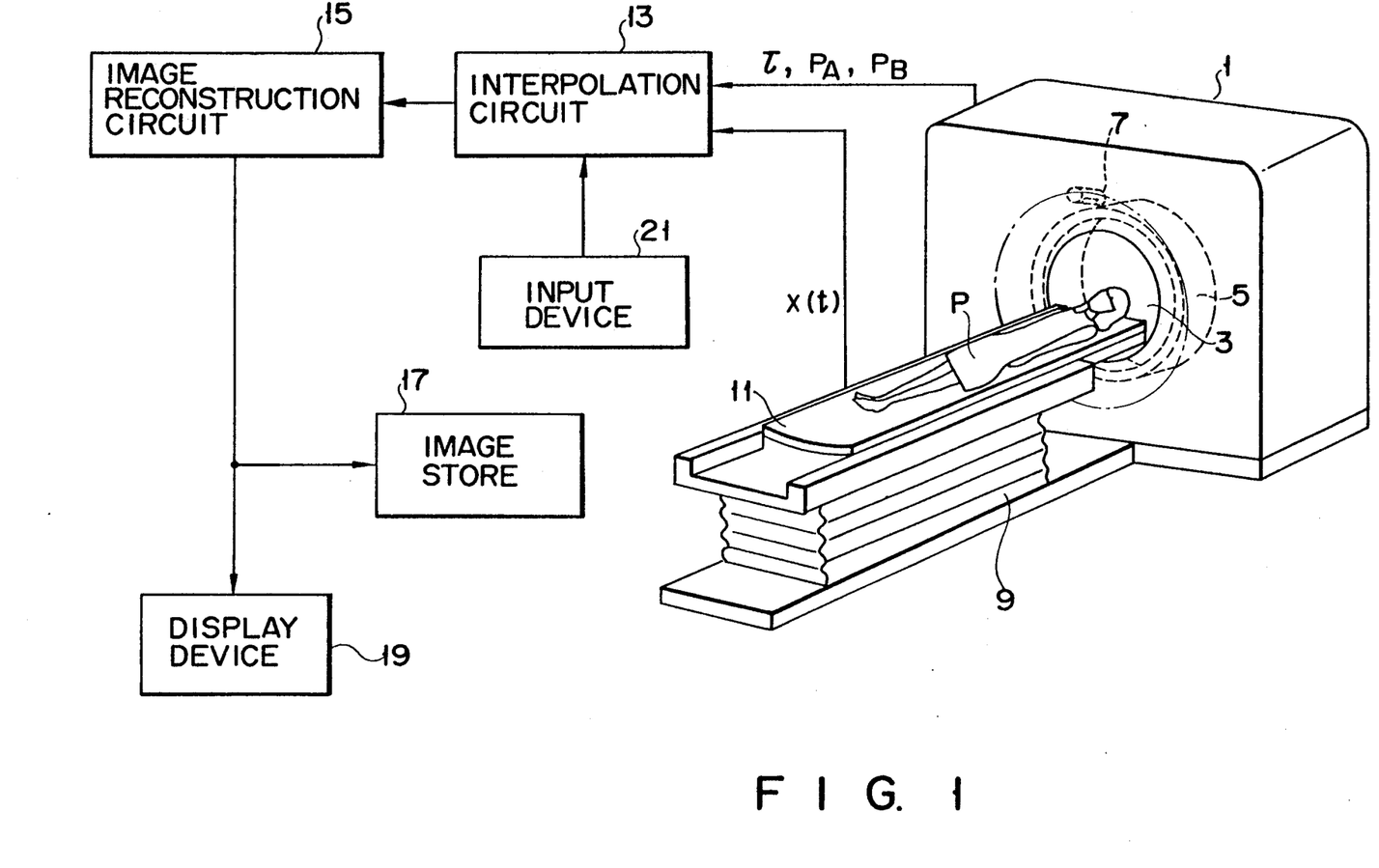
FIG. 1 is a block diagram of a CT apparatus according to a first embodiment of the present invention.

Embodiments of a CT apparatus according to the present invention will now be described with reference to the accompanying drawings. FIG. 1 is a block diagram of a first embodiment of an X-ray CT apparatus according to the present invention. A housing dome 1, which incorporates an X-ray tube, a detector and other components, has its center portion open cylindrically in the horizontal direction to define a scanning space 3. Within the dome around the space 3 is provided a detector array 5 which has many X-ray detectors arranged circumferentially. An X-ray tube 7 is disposed rotatably around the array 5. The X-ray tube 7 can be continuously rotated by using a slip ring. This scan system is a modification of a so-called fourth generation scan system which has detectors arranged circumferentially and an X-ray tube disposed rotatably inward of the detector arrangement. A gantry assembly 9 is connected to the front of the dome 1, and a patient platform 11 on which an object P is placed slides on the gantry assembly 9 to carry the object P into the scanning space 3.

When the patient platform 11 carrying the object P slides in the space 3, the X-ray tube 7 irradiates a fan-shaped X-ray onto the object P while rotating around the imaginary axis which passes the center of the space 3 and lies within the object P. By moving the patient platform 11 and rotating the X-ray tube 7 at the same time, the object P is scanned helically with X-rays. The detector array 5 detects the X-rays from the X-ray tube 7 which have penetrated the object P. Because the X-ray tube 7 is located outside the detector array 5, there are two detectors positioned along the radiation path of the X-rays, one closest to the tube 7 and the other opposite to the former one. In order to turn the closest detector off, therefore, the array 5 performs a nutation movement when X-rays are irradiated. Therefore, this system is called a nutation/rotation system.

Since the continuous rotation and the nutation/rotation system can permit movement of the patient platform and rotation of the X-ray tube both continuously without interruption, the helical scan can be easily realized. It is noted that even with the use of the so-called third generation and fourth generation scanning systems in which the X-ray tube is not continuously rotated, the helical scan can be executed if the sliding of the patient platform is performed when X-ray irradiation occurs. Further, the helical scan can be executed with the use of the third generation scanning system having a slip ring.

A detection signal from the detector array 5 is output from the dome 1 and is supplied to an interpolation circuit 13. This circuit 13 is also supplied with a signal from the dome 1 which represents the rotational velocity (rotational cycle $\tau$) of the X-ray tube 7, as well as a signal from the gantry assembly 9 which represents the scanning position x(t) of the patient platform 11. The interpolation circuit 13 performs a pre-processing, such as amplification, integration, or D/A conversion, on the detection signal obtained by the detector array 5, thereby calculating a projection data point for each projection angle. Based on the rotational velocity data of the X-ray tube 7 and the scanning position data of the patient platform 11, the interpolation circuit 13 performs interpolation processing (to be described later) on the projection data acquired by the helical scan, and outputs interpolation data which is equivalent to the projection data acquired when the X-ray tube is rotated within the same slice of the object.

Figure 2:
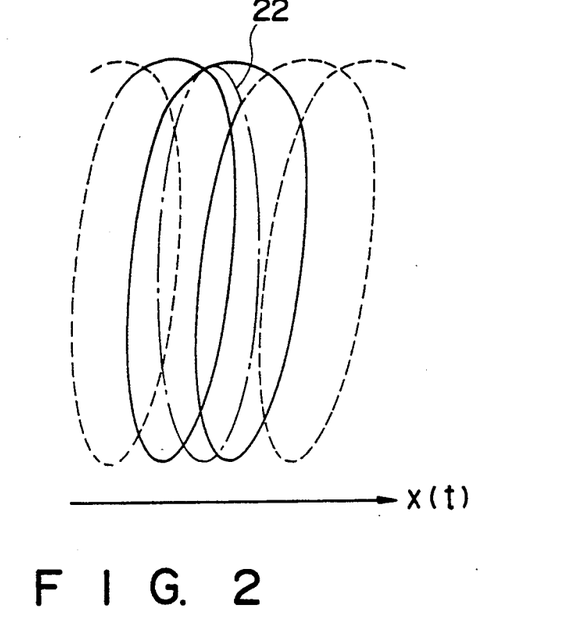
FIG. 2 is a diagram illustrating a locus of movement of an X-ray tube in the helical scan.

In the helical scan, if it is assumed that the object is fixed, the locus of the relative movement of the X-ray tube 7 to the object becomes helical as indicated by the broken line and the solid line in FIG. 2. This helical scan data does not therefore include projection data of one slice. Rather, the interpolation circuit 13 acquires, through interpolation, projection data for 360° of a predetermined slice as indicated by the one-dot chain line 22 as shown in FIG. 2 from the helical scan data for two turns indicated by the solid line.

The projection data interpolation data) from the interpolation circuit 13 is supplied to an image reconstruction circuit 15 where image reconstruction is performed. Reconstructed image data is supplied to and stored in an image store 17 which uses a recording medium such as a hard disk. The image data is also supplied to a display device 19 comprising a CRT which in turn displays a slice image, or the like, of the object P. The embodiment further comprises an input device 21, such as a keyboard, through which a scanning position for specifying a slice for which interpolation data is to be acquired, is entered.

Figure 3:
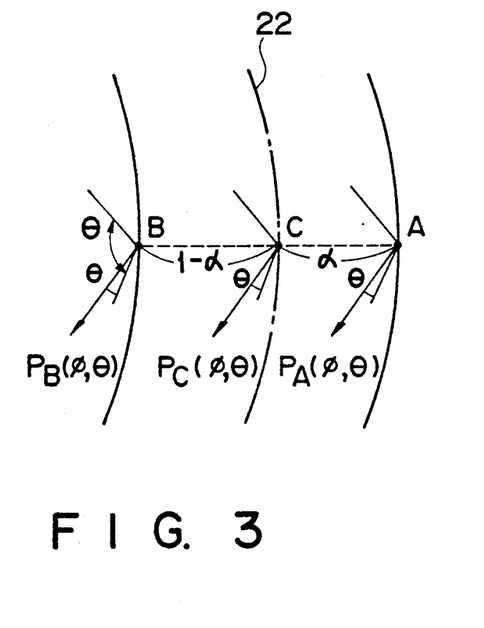
FIG. 3 is a diagram illustrating the interpolation principle according to the present invention.

A description will now be given of the principle of the interpolation carried out by the interpolation circuit 13. The interpolation circuit 13 acquires interpolation data for each point on a slice 22 shown in FIG. 3 by performing linear interpolation of scan data of two adjoining points on the helix which have the same projection angle. FIG. 3 shows the locus of the X-ray tube which is also the locus of the detectors. In practice, projection data is obtained for each channel $\theta$. The channel is part of a fan-shaped X-ray beam and is expressed by the following equation:

$$\theta = \Delta\theta \cdot i \qquad (1)$$

$\Delta\theta$ is a channel pitch and i is the number of detector channels ($1 \leq i \leq$ total number of detectors of the detector array 5).

The interpolation circuit 13 calculates interpolation data $P_C(\phi, \theta)$ of a point C on the slice 22, using projection data $P_A(\phi, \theta)$ and $P_B(\phi, \theta)$ of two adjacent points A and B on the helix which have the same projection angle $\phi$ as the point C and an interpolation ratio $\alpha$ as follows.

$$P_C(\phi, \theta) = \alpha \cdot P_A(\phi, \theta) + (1-\alpha) \cdot P_B(\phi, \theta) \qquad (2)$$

$\alpha$ is expressed by the ratio of the differences between the scanning positions $X_A$, $X_B$, and $X_C$ of the points A, B, and C as follows.

$$\alpha = (X_C - X_B)/(X_A - X_B) \qquad (3)$$

Figure 5:
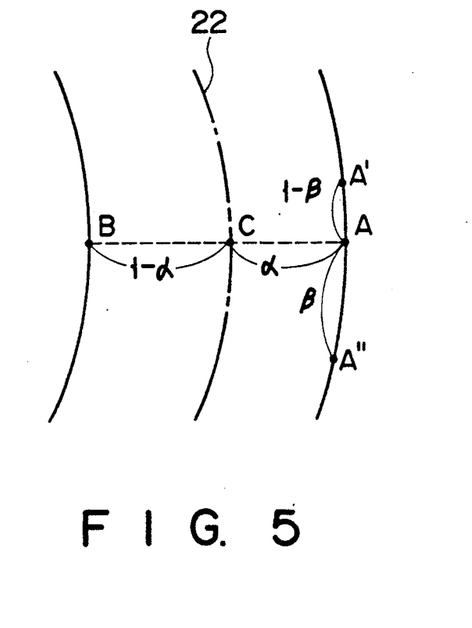
FIG. 5 is a diagram illustrating an interpolation technique when the speed of the helical scan is not constant.

If either the rotational velocity of the X-ray tube 7 or the sliding speed of the patient platform is not constant, there may be no projection data at the adjacent point, for example, the point A as shown in FIG. 5. To properly deal with this case, first projection data of point A is obtained through interpolation from projection data of two points A' and A" in the proximity of the point A. The interpolation ratio $\beta$ in this case can be acquired from the projection angles of individual points A', A, and A". For the subsequent computation, the computations previously described can be used.

Figure 4:
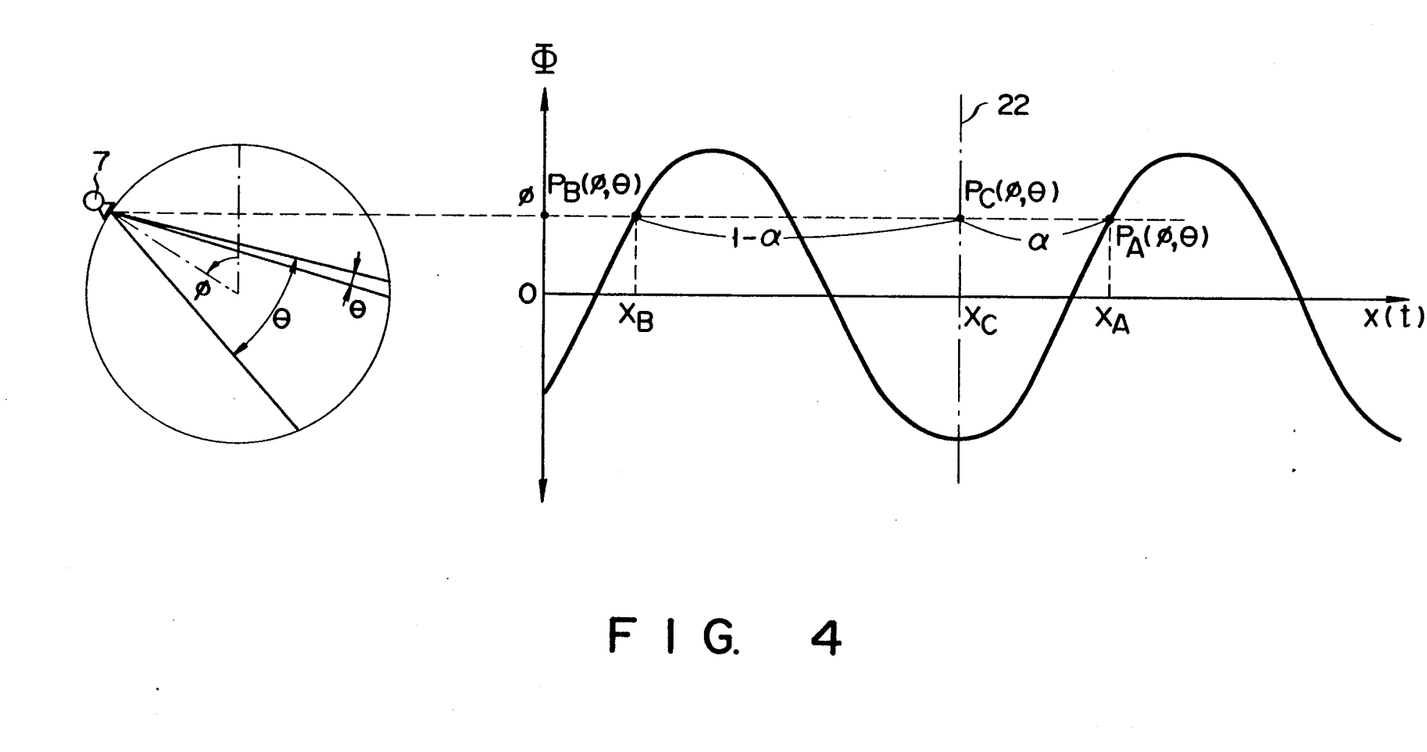
FIG. 4 is a diagram giving a detailed illustration of the principle shown in FIG. 3.

The operation of this embodiment will be described below. Scanning position XC (see FIG. 4) or the like corresponding to a target slice whose slice image is desired, is entered via the input device 21. The X-ray tube 7 is rotated at a given cycle $\tau$ while sliding the patient platform 11 on which the object P is placed at a constant velocity to carry the body P inside the scanning space 3, whereby the object P is helically scanned at a constant velocity. Helical scan data obtained by this helical scan is supplied, together with rotational cycle data of the X-ray tube 7 and scanning position data of the patient platform 11 from the gantry assembly 9, to the interpolation circuit 13. This circuit 13 performs the aforementioned various pre-processing on the helical scan data to provide projection data, then performs interpolation of this projection data according to the aforementioned equation (2) to thereby acquire a projection data point for each projection angle in the slice 22 for each channel. The interpolation data is supplied to the image reconstruction circuit 15 where image reconstruction is executed. The resultant image data is sent to, and stored in, the image store 17. This image data is also supplied to the display device 19 which, based on the interpolation data, displays the image of a desired slice of the object.

According to this embodiment, projection data on a desired slice can be interpolated from data of the adjacent two points on a helix having the same projection angle in accordance with the distances between the two points and the desired slice. Accordingly, a slice image without artifact can be obtained. Even if the moving velocity of the patient platform and the rotational velocity of the X-ray tube are increased to ensure a high helical scan, the aforementioned interpolation can be executed, thus preventing any artifact from occurring. Further, the spatial resolution in the moving direction of the patient platform 11 is increased, since the slice image of the arbitrary scanning position can be obtained.

Figure 6:
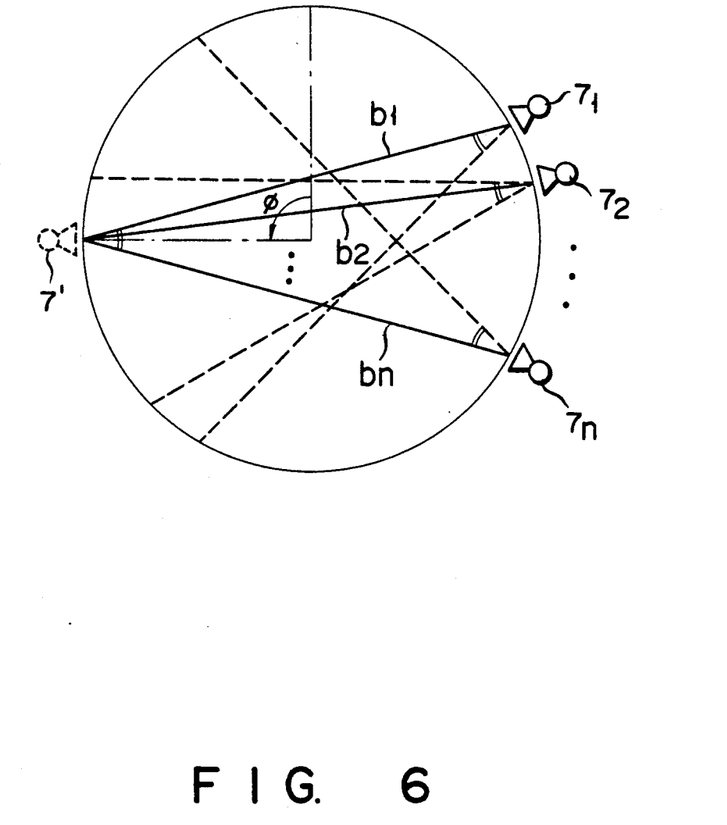
FIG. 6 is a view explaining projection data formed by counter beams which is used in a second embodiment of the present invention.

A second embodiment utilizing projection data formed of counter beams will now be described. The X-ray beam transmitted through the object in one direction and the counter X-ray beam transmitted through the object in the opposite direction have the same projection data. Therefore, as shown in FIG. 6, even if the X-ray tube 7' does not irradiate the X-rays at the projection angel $\phi$, the projection data having the projection angle $\phi$ can be obtained by the X-ray counter beams $b_1$, $b_2$, ... $b_n$ irradiated from the Xray tubes $7_1$, $7_2$, ... $7_n$.

Figure 7:
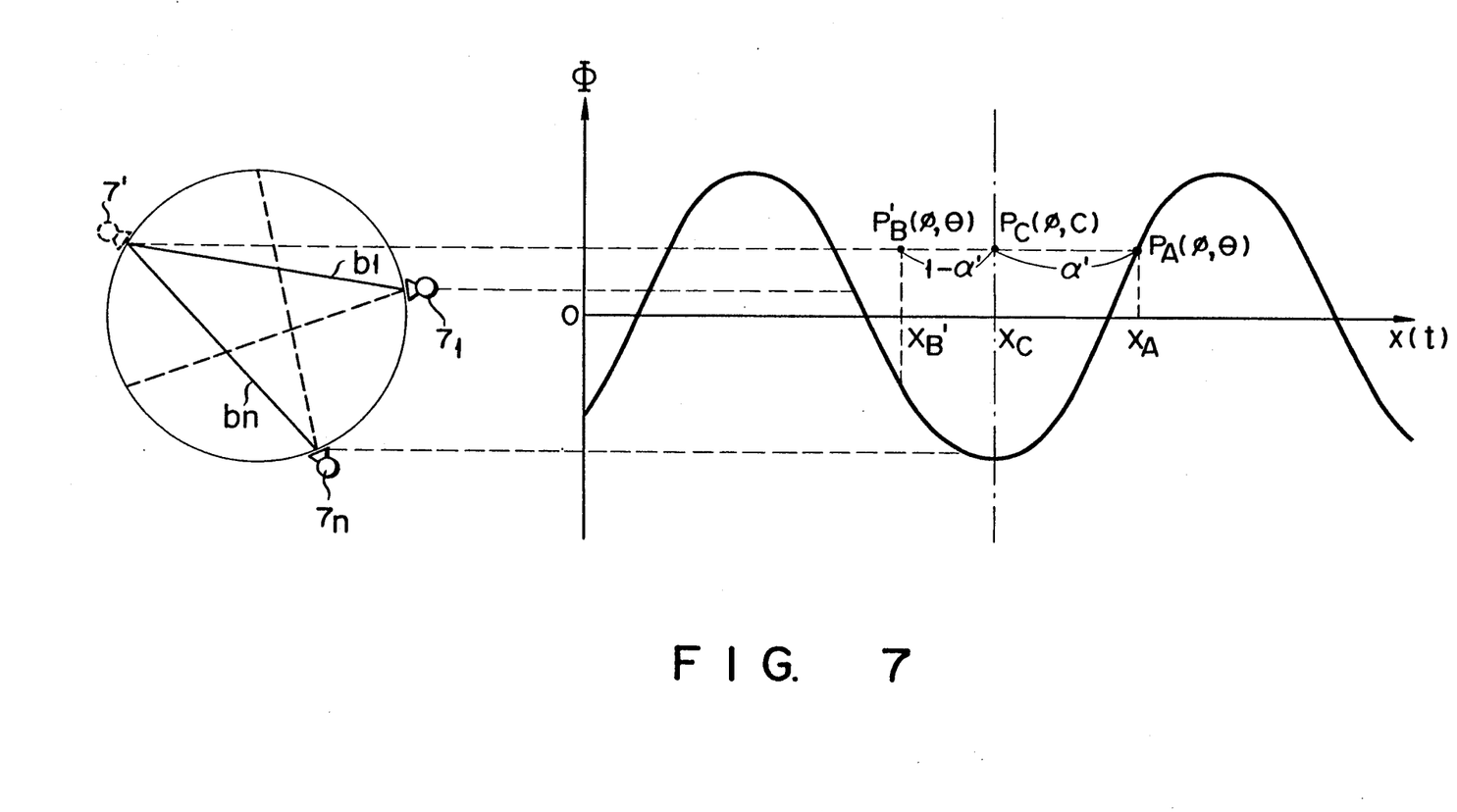
FIG. 7 is a diagram illustrating the interpolation principle according to the second embodiment.

The block diagram of the second embodiment is the same as that of the first embodiment. The interpolation principle using the counter beams according to the second embodiment is shown in FIG. 7. In the second embodiment, the interpolation circuit 13 first calculates the projection data having the projection angel $\phi$ from the counter beams $b_1$, $b_2$, ... $b_n$. Then, the interpolation circuit 13 calculates interpolation data $P_C(\phi, \theta)$ of a point C on the slice 22, using projection data $P_A(\phi, \theta)$ and $P'_B(\phi, \theta k)$ of the two scanning positions $X'_B$ and $X_A$ on the helix. The scanning position $X'_B$ corresponds to the middle point between the scanning position of the X-ray tube $7_1$ and that of the X-ray tube $7_n$. The interpolation is expressed as follows.

$$P_C(\phi, \theta) = \alpha' \cdot P_A(\phi, \theta) + (1 - \alpha') \cdot P_B(\phi, \theta) \quad (4)$$

$\alpha'$ is expressed by the ratio of the differences between the scanning positions $X_A$, $X'_B$, and $X_C$ as follows.

$$\alpha' = (X_C - X'_B)/(X_A - X'_B) \quad (5)$$

According to the second embodiment, the projection data obtained by using the counter beams has a scanning position $X'_B$ which is closer to the desired position $X_C$ than the position $X_B$ as in the first embodiment. Therefore, the interpolation includes less error due to the difference of the scanning position.

The present invention is not limited to the above-described embodiment, but may be modified in various manners. Although the foregoing description of the embodiment has been given with reference to an X-ray CT apparatus, radiation rays are not restricted to X-rays but may take another form, such as gamma rays. The practical method for realizing the helical scan is not limited to what has been described above, and the arrangement of the X-ray tube and detectors can be appropriately altered. Further, although the helical scan velocity determined in accordance with the moving velocity of the patient platform and rotational velocity of the X-ray tube are assumed to be constant in one embodiment, they need not necessarily be constant as long as these velocities are known, since the distance between points in different slices can be acquired on the basis of the scan velocity.

Although the interpolation data for a slice is acquired from data of two points through a linear interpolation of the first order, it may be acquired through a nonlinear interpolation of the second order or greater or through a spline interpolation. Further, it is possible to interpolate the projection data of the desired slice from more than two data having the same projection angle.

As described above, according to the present invention, projection data equivalent to that acquired when the same slice is scanned can be obtained by interpolating data obtained by a helical scan, thereby eliminating any artifact which is the shortcoming of the conventional helical scan.

Additional advantages and modifications will readily occur to those skilled in the art. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents.

What is claimed is:

1. A computerized tomographic apparatus comprising:

scanning means for moving an object in a direction, for producing and rotating radiation rays within a plane intersecting the direction of movement to perform a helical scan on said object, and for receiving a plurality of sets of projection data points, each set of projection data points corresponding to a 360° portion of a helix in the object;

first interpolation means, coupled to the scanning means, for calculating a set of output data points corresponding to a desired slice of the object, an output data point of the desired slice being calculated by determining a first projection data point from a first adjacent 360° portion of the helix and a second projection data point from a second adjacent 360° portion of the helix located on both sides of the desired slice, both projection data points having the same desired projection angle as that of the output data point, and by interpolating the distances between each of the first and second projection data points and a plane containing the desired slice to determine the output data point; and second interpolation means for calculating one of the projection data points if either set of projection data points corresponding to the first or second 360° portions of the helix does not include a projection data point having the desired projection angle by interpolating a third projection data point and a fourth projection data point, the third and fourth projection data points being located on the 360° portion of the helix which does not include a projection data point having the desired projection angle, and the third and fourth projection data point having projection angles adjacent to the desired projection angle.

2. An apparatus according to claim 1, wherein said first interpolation means calculates the desired output data point $P_C(\phi, \theta)$ of the desired slice having a projection angle $\phi$ by processing two projection data points $P_A(\phi, \theta)$ and $P_B(\phi, \theta)$ of the first and second adjacent 360° portions of a helix, both projection data points having the projection angle $\phi$ as follows:

$$P_C(\phi, \theta) = \alpha \cdot P_A(\phi, \theta) + 1 - \alpha) \cdot P_B(\phi, \theta)$$

where $\alpha$ is an interpolation ratio and is expressed as follows:

$$\alpha = (X_C - X_B)/(X_A - X_B)$$

where $X_A - X_B$ and $X_C - X_B$ are respectively the distance between the first and second 360° portions of the helix and the distance between the desired slice and the 360° portion of the helix which corresponds to projection data point $P_B(\phi, \theta)$.

3. An apparatus according to claim 1, wherein said first interpolation means comprises:

means for calculating a second projection data point $P'_B(\phi, \theta)$ of a first 360° portion of the helix having a projection angle $\phi$ from counter beams; and means for calculating the output data point $P_C(\phi, \theta)$ of the desired slice having the projection angle $\phi$ by interpolating the first projection data point $P_A(\phi, \theta)$ of a second 360° portion of the helix having the projection angle $\phi$ and the projection data $P'_B(\phi, \theta)$ of the first slice as follows:

$$P_C(\phi, \theta) = \alpha' \cdot P_A(\phi, \theta) + (1-\alpha') \cdot P'_B(\phi, \theta)$$

where $\alpha'$ is an interpolation ration and is expressed as follows: $\alpha' = (X_{C]} - X'_B)/(X_A - X'_B)$ where $X_A - X'_B$ and $X_C - X'_B$ are respectively the distance between the first and second 360° portions of the helix and the distance between the desired slice and the first 360° portion of the helix.

4. An apparatus according to claim 1, further comprising:

image reconstruction means for processing an output of said first and said second interpolation means; and means for displaying an output of said image reconstruction means.

5. A method for providing a slice image of an object, comprising the steps of:

moving said object in a direction while rotating radiation rays within a plane intersecting the direction of movement to perform a helical scan on said object, thereby providing a plurality of sets of projection data points, each set of projection data points corresponding to a 360° portion of a helix in the object;

designating a desired slice of said object;

interpolating to calculate a desired output data point in the desired slice having a given projection angle by processing a first projection data point located in a first 360° portion of the helix and a second projection data point located in a second 360° portion of the helix located on both sides of the desired slice and by processing a distance between the first and second 360° portions of the helix and the desired slice;

calculating one of the projection data points if either set of projection data points corresponding to the first or second 360° portions of the helix does not include a projection data point having the desired projection angle by interpolating a third projection data point and a fourth projection data point, the third and fourth projection data points being located on the 360° portion of the helix which does not include a projection data point having the desired projection angle, and the third and fourth projection data point having projection angles adjacent to the desired projection angle; and reconstructing an image based on the desired projection data obtained by said interpolation.

6. A computerized tomographic apparatus comprising:

means for helically scanning an object and providing a plurality of sets of projection data points along a helical line;

means for interpolating a first and a second projection data point to generate an output data point having a given projection angle;

means for sampling the first projection data point having the given projection angle from a first 360° portion of the helical line and the second projection data point having the given projection angle from a second 360° portion of the helical line, the first and second 360° portions being adjacent to and located on both sides of a desired slice of the object;

means for calculating the first projection data point if the first 360° portion does not include a projection data point having the given projection angle by interpolating a third projection data point and a fourth projection data point, the third and fourth projection data points being located on the first 360° portion of the helix; and means for reconstructing an image of the desired slice based on a plurality of the output data points of the desired slice obtained from said interpolating means.

7. An apparatus according to claim 6, wherein said sampling means and interpolating means interpolate the projection data through a linear interpolation system.

8. An apparatus according to claim 6, wherein said sampling means and interpolating means interpolate the projection data through a nonlinear interpolation system.

9. An apparatus according to claim 6, wherein said sampling means and interpolating means interpolate the projection data through a spline interpolation system.

10. An apparatus according to claim 6, wherein said third and fourth projection data points have projection angles closer to the given projection angle than any other projection data points on the first 360° portion.

* * * * *

UNITED STATES PATENT AND TRADEMARK OFFICE
CERTIFICATE OF CORRECTION

PATENT NO. : 5,073,911
DATED : December 17, 1991
INVENTOR(S) : Masahiro Ozaki et al.

It is certified that error appears in the above-identified patent and that said Letters Patent is hereby corrected as shown below:

Column 7, claim 3, line 16, change "ration" to --ratio--.

Column 7, claim 3, line 17, change "$\alpha' = (X_C[-$" to $--\alpha' = (X_C- --$.

Signed and Sealed this

Twenty-second Day of June, 1993

Attest:

MICHAEL K. KIRK

Attesting Officer     Acting Commissioner of Patents and Trademarks